United States Patent [19]

Becker et al.

[11] Patent Number: 4,650,513
[45] Date of Patent: Mar. 17, 1987

[54] CYCLOHEXENONES AND THEIR USE FOR CONTROLLING UNDESIRABLE PLANT GROWTH

[75] Inventors: Rainer Becker, Bad Duerkheim; Dieter Jahn, Edingen-Neckarhausen; Ulrich Schirmer, Heidelberg; Michael Keil, Freinsheim; Bruno Wuerzer, Otterstadt; Norbert Meyer, Ladenburg, all of Fed. Rep. of Germany

[73] Assignee: BASF Aktiengesellschaft, Fed. Rep. of Germany

[21] Appl. No.: 708,933

[22] Filed: Mar. 6, 1985

[30] Foreign Application Priority Data

Mar. 6, 1984 [DE] Fed. Rep. of Germany ....... 3408153
Mar. 22, 1984 [DE] Fed. Rep. of Germany ....... 3410492

[51] Int. Cl.$^4$ .................. C07D 333/22; A01N 309/04
[52] U.S. Cl. ........................... 71/88; 549/331; 549/333; 549/13; 549/14; 71/90; 71/94; 71/91; 71/124; 71/113; 546/16; 564/256; 562/500
[58] Field of Search .......................... 549/331; 71/88

[56] References Cited

U.S. PATENT DOCUMENTS 3,950,420  4/1976  Sawaki et al. ........................ 71/88
3,989,737 11/1976  Sawaki et al. ........................ 560/62
4,422,864 12/1983  Becker et al. ........................ 71/88
4,511,391  4/1985  Serben et al. ........................ 71/88
4,545,806 10/1985  Jahn et al. ........................... 71/88

FOREIGN PATENT DOCUMENTS 63052    5/1979  Japan .
183746  11/1982  Japan .
144384   8/1983  Japan .
2090246  7/1982  United Kingdom .

OTHER PUBLICATIONS

Buyck et al., Tetrahedron Lett. 29, 2491 (1975).

Primary Examiner—Nicky Chan
Attorney, Agent, or Firm—Keil & Weinkauf

[57] ABSTRACT

Cyclohexenones of the formula

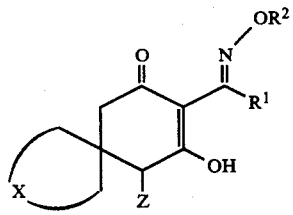

where $R^1$ is alkyl, $R^2$ is alkyl, alkenyl, alkynyl, or haloalkyl, Z is hydrogen or alkoxycarbonyl, and X is a substituted or unsubstituted pentamethylene chain in which one or two methylene groups can be replaced by O, S, SO, $SO_2$ or $NR^3$, and their use for controlling undesirable plant growth.

7 Claims, No Drawings

CYCLOHEXENONES AND THEIR USE FOR CONTROLLING UNDESIRABLE PLANT GROWTH

The present invention relates to cyclohexenones, their preparation, and herbicides which contain these compounds as active ingredients.

Japanese Preliminary Published Appilictions Nos. 82/183 746 and 83/144 384 disclose that spirocyclic cyclohexenones possess herbicidal activity.

We have found that cyclohexenones of the formula

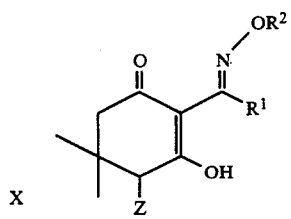

wherein $R^1$ is $C_1$-$C_4$-alkyl, $R^2$ is $C_1$-$C_4$-alkyl, $C_3$-$C_5$-alkynyl or unsubstituted or halogen-substituted $C_3$-$C_5$-alkenyl, Z is hydrogen or $C_2$-$C_5$-alkoxycarbonyl and X is a pentamethylene chain which is unsubstituted or substituted by $C_1$-$C_4$-alkyl, $C_1$-$C_4$-alkoxy or $C_1$-$C_4$-alkylthio and in which one or two methylene groups may be replaced by O, S, SO, $SO_2$ or $NR^3$, where $R^3$ is $C_1$-$C_4$-alkyl, $C_2$-$C_7$-acyl or benzyl, with the proviso that one substituent from the group consisting of alkyl, alkoxy and alkylthio is present when X is pentamethylene, and the crop-tolerated salts of these compounds, exhibit a good herbicidal action, preferably against species from the grasses famil (Gramineae). They are tolerated by, and hence have a selective action in, broad-leaved crops and in monocotyledon crops which do not belong to the Gramineae.

The cyclohexenones of the formula I can occur in tautomeric forms, all of which are embraced by the claims:

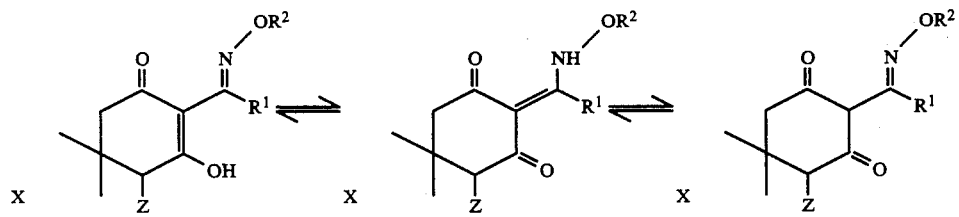

In formula I, $R^1$ is straight-chain or branched $C_1$-$C_4$-alkyl eg. methyl, ethyl, n-propyl, sec-butyl or isobutyl, $R^2$ is straight-chain or branched $C_1$-$C_4$-alkyl, $C_3$-$C_5$-alkynyl or unsubstituted or halogen-substituted, in particular chlorine-substituted, $C_3$-$C_5$-alkenyl, eg. ethyl, propyl, allyl, propargyl, 3-chloroallyl (cis or trans) or 2-chloroallyl, Z is hydrogen or $C_2$-$C_5$-alkoxycarbonyl, eg. methoxycarbonyl or ethoxycarbonyl, and X is a pentamethylene chain in which one or two methylene groups can be replaced by O, S, SO, $SO_2$ or $NR^3$. This radical may be unsubstituted or substituted by one or more radicals from the group consisting of $C_1$-$C_4$-alkyl, $C_1$-$C_4$-alkoxy and $C_1$-$C_4$-alkylthio, eg. methyl, ethyl, n-propyl, sec-butyl, isobutyl, methoxy, ethoxy, n-propoxy, n-butoxy, methylthio, ethylthio, isopropylthio or sec-butylthio. If X is pentamethylene, a substituent from the group consisting of alkyl, alkoxy and alkylthio must be present. In $NR^3$, $R^3$ is $C_1$-$C_4$-alkyl, $C_2$-$C_7$-acyl or benzyl, eg. methyl, ethyl, acetyl, propionyl, benzoyl or benzyl. X is, for example, —$CH_2CH(SCH_3)CH_2CH_2CH_2$—, —$CH_2CH(SC_2H_5)CH_2CH_2CH_2$—,
—$CH_2CH(COCH_3)CH_2CH_2CH_2$—,
—$CH_2CH(OC_2H_5)CH_2CH_2CH_2$—,
—$CH_2CH_2CH(CH_3)CH_2CH_2$—, —$CH_2CH_2OCH_2CH_2$—,
—$CH_2CH_2SCH_2CH_2$—, —$CH_2CH_2SOCH_2CH_2$—,
—$CH_2OCH_2OCH_2$—, —$CH_2CH_2SO_2CH_2CH_2$—,
—2$SCH_2CH_2$—, —$CH_2SOCH_2CH_2CH_2$—,
—$CH_2SO_2CH_2CH_2CH_2$—, —$CH_2SCH_2SCH_2$—,
—$CH_2SCH(CH_3)SCH_2$—, —$CH_2SC(CH_3)_2SCH_2$—,
$CH_2CH_2NCH_3CH_2CH_2$—, —$CH_2CH_2N(COCH_3)CH_2CH_2$—,
—$CH_2CH_2N(CH_2C_6H_5)CH_2CH_2$—, or
—$CH_2CH_2N(COC_6H_5)CH_2CH_2$—.

Examples of suitable salts of the cyclohexenones of the formula I are the alkali metal salts, in particular the potassium or sodium salts, alkaline earth metal salts, in particular calcium salts, magnesium salts or barium salts, manganese salts, copper salts, zinc salts and iron salts, as well as ammonium, phosphonium, sulfonium and sulfoxonium salts, for example ammonium, tetraalkylammonium, benzyltrialkylammonium, trialkylsulfonium, or trialkylsulfoxonium salts.

Preferred cyclohexenones of the formula I are those in which Z is hydrogen, or those in which X is an oxapentamethylene or thiapentamethylene chain.

The compounds of the formula I can be obtained by reacting a compound of the formula

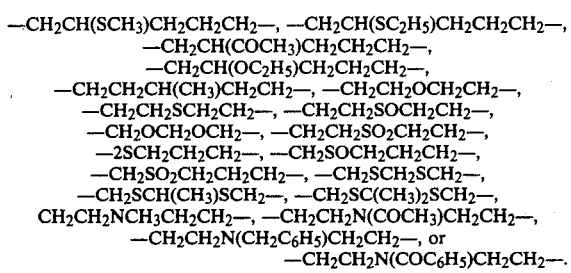

where $R^1$, Z and X have the above meanings, with a hydroxylamine derivative $R^2O$—$NH_3Y$, where $R^2$ has the above meanings and Y is an anion.

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction takes place particularly readily at a pH of from 2 to 9, in particular from 4.5 to 5.5, the pH advantageously being set by adding an acetate, for example an alkali metal acetate, in particular sodium acetate or potassium acetate or a mixture of the two salts. Alkali metal acetates are added in amounts of, for example, from 0.5 to 2 moles, based on the ammonium compound of the formula $R^2O-NH_3Y$.

Examples of suitable solvents are dimethyl sulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the product can then be isolated by evaporating down the mixture, adding water, extracting with a non-polar solvent, such as methylene chloride, and distilling off the solvent under reduced pressure.

The compounds of the formula I can furthermore be obtained by reacting a compound of the formula II with a hydroxylamine of the formula $R^2O-NH_2$, where $R^2$ has the above meanings, in an inert diluent at from 0° C. to the boiling point of the reaction mixture, in particular from 15° to 70° C. If necessary, the hydroxylamine can be used in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetronitrile, and cyclic ethers, such as tetrahydrofuran.

The compounds of the formula I can also be obtained by reacting a compound of the formula II with an unsubstituted hydroxylammonium salt $NH_2OH.HY$, where Y has the above meaning, with the addition of a solvent and an auxiliary base, at from 0° to 80° C., to give an oxime of the formula

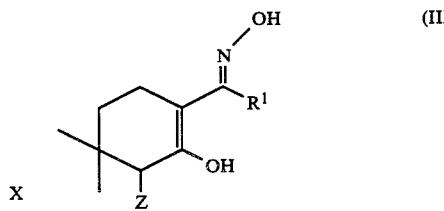

(III)

where $R^1$, X and Z have the above meanings, and further reacting this product with an alkylating agent of the formula $R^2Y'$, where $R^2$ has the above meanings and $Y'$ is a leaving group.

Suitable solvents are those listed for the reaction of the compounds of the formula II with hydroxylamines, and suitable bases are the basic substances stated for the reaction of the compounds of the formula II with hydroxylamine derivatives of the formula $R^2O-NH_3Y$, twice the amount of base being required in this case.

The alkali metal salts of the compounds of the formula I can be obtained by treating these compounds with sodium hydroxide or potassium hydroxide in aqueous solution or in an organic solvent, such as methanol, ethanol or acetone. Sodium alcoholates and potassium alcoholates can also be used as bases.

The remaining metal salts, eg. the manganese, copper, zinc, iron, calcium, magnesium and barium salts can be prepared from the sodium salts by reaction with the corresponding metal chlorides in aqueous solution. Ammonium and phosphonium salts can be obtained by reacting compounds of the formula I with ammonium, phosphonium, sulfonium or sulfoxonium hydroxides, if appropriate in aqueous solution.

The compounds of the formula II can be prepared from cyclohexane-1,3-diones of the formula IV by a conventional method (Tetrahedron Lett. 29, (1975), 2491), the said cyclohexane-1,3-diones also occurring in the tautomeric form IV a

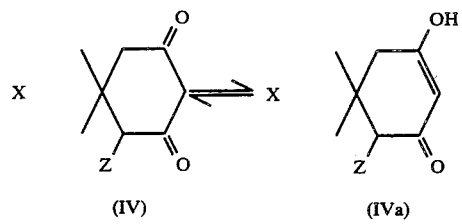

(IV)    (IVa)

It is also possible to prepare compounds of the formula II via the enol-ester intermediates, which are obtained in the reaction of compounds of the formula IV and undergo rearrangement in the presence of an imidazole or pyridine derivative (Japanese Preliminary Published Application No. 79/063052).

The compounds of the formula IV are obtained by conventional processes, as can be seen from the equation below:

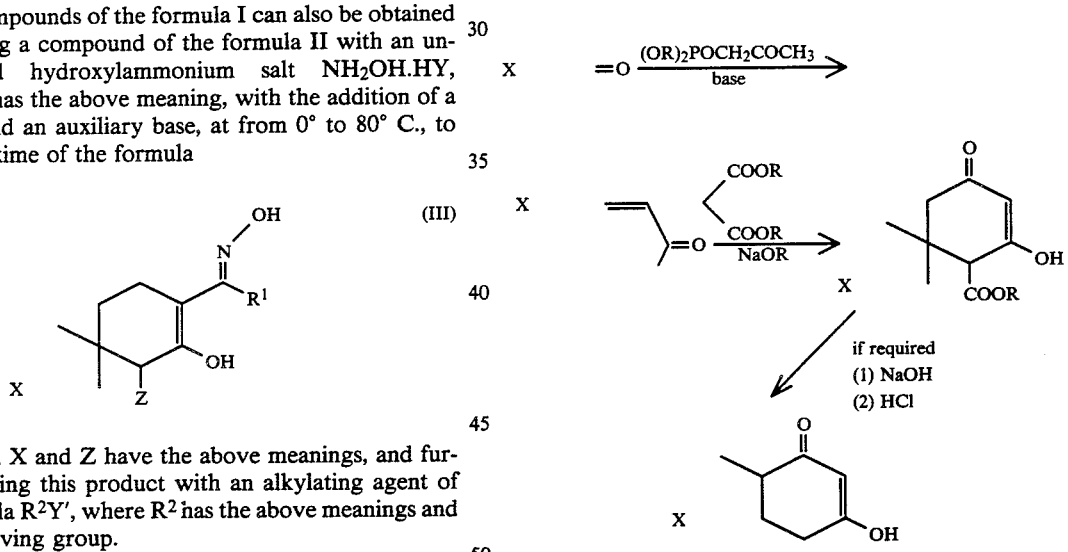

The Example which follows illustrates the preparation of the cyclohexenones of the formula I.

EXAMPLE 9.7 parts by weight of 9-butyryl-3-oxaspiro[5.5]undecane-8,10-dione are taken up in 100 parts by volume of ethanol, and 3.57 parts by weight of sodium bicarbonate are added. After the addition of 4.13 parts by weight of ethoxyaminohydrochloride, the reaction mixture is stirred for about 20 hours at 20° C. and then poured into ice water/methylene chloride, and the organic phase is separated off and evaporated down. 10.9 parts by weight of 9-(1-ethoxyimino-n-butyl)-3-oxaspiro[5.5]undecane-8,10-dione of melting point 74°-76° C. remain (compound No. 1).

The following cyclohexenone derivatives of the formula I can be prepared by the same route:

| Compound no. | X | Z | $R^1$ | $R^2$ | M.p.[°C.]/$n_D$ (°C.)/$^1$H—NMR data |
|---|---|---|---|---|---|
| 1 | $CH_2CH_2OCH_2CH_2$ | H | $n\text{-}C_3H_7$ | $C_2H_5$ | 74–76 |
| 2 | $CH_2CH_2OCH_2CH_2$ | H | $n\text{-}C_3H_7$ | allyl | 1.5317 (22) |
| 3 | $CH_2CH_2OCH_2CH_2$ | $COOCH_3$ | $n\text{-}C_3H_7$ | $C_2H_5$ | |
| 4 | $CH_2OCH_2CH_2CH_2$ | H | $n\text{-}C_3H_7$ | $C_2H_5$ | |
| 5 | $CH_2OCH_2CH_2CH_2$ | H | $n\text{-}C_3H_7$ | allyl | |
| 6 | $CH_2SCH_2CH_2CH_2$ | H | $n\text{-}C_3H_7$ | $C_2H_5$ | 1.5522 (22) |
| 7 | $CH_2SCH_2CH_2CH_2$ | $COOC_2H_5$ | $n\text{-}C_3H_7$ | $C_2H_5$ | |
| 8 | $CH_2SCH_2CH_2CH_2$ | H | $n\text{-}C_3H_7$ | allyl | 1.5572 |
| 9 | $CH_2SCH_2CH_2CH_2$ | H | $n\text{-}C_3H_7$ | 3-chloroallyl (trans) | 1.5657 |
| 10 | $CH_2SOCH_2CH_2CH_2$ | H | $n\text{-}C_3H_7$ | $C_2H_5$ | |
| 11 | $CH_2SO_2CH_2CH_2CH_2$ | H | $n\text{-}C_3H_7$ | $C_2H_5$ | |
| 12 | $CH_2SO_2CH_2CH_2CH_2$ | H | $n\text{-}C_3H_7$ | allyl | |
| 13 | $CH_2CH(SEt)CH_2CH_2CH_2$ | H | $n\text{-}C_3H_7$ | $C_2H_5$ | 0.95 (t, 3H); 1.2 (t, 3H); 1.32 (t, 3H); 2.53 (q, 2H); 2.9 (t, 2H); 4.1 (q, 2H); 15 (s, 1H) |
| 14 | $CH_2CH(SEt)CH_2CH_2CH_2$ | H | $n\text{-}C_3H_7$ | allyl | 0.95 (t, 3H); 1.2 (t, 6H), 2.9 (t, 2H), 4.5 (d, 2H), 5.35 (dd, 2H); 5.9–6.1 (m, 1H) |
| 15 | $CH_2CH(OCH_3)CH_2CH_2CH_2$ | H | $n\text{-}C_3H_7$ | $C_2H_5$ | |
| 16 | $CH_2CH(OCH_3)CH_2CH_2CH_2$ | H | $n\text{-}C_3H_7$ | allyl | |
| 17 | $CH_2CH_2CH(CH_3)CH_2CH_2$ | H | $n\text{-}C_3H_7$ | $C_2H_5$ | |
| 18 | $CH_2SCH_2SCH_2$ | H | $C_2H_5$ | $C_2H_5$ | 76–80 |
| 19 | $CH_2SCH_2SCH_2$ | H | $C_2H_5$ | allyl | 1.5954 (22) |
| 20 | $CH_2SCH_2SCH_2$ | H | $n\text{-}C_3H_7$ | $C_2H_5$ | 80–82 |
| 21 | $CH_2SCH_2SCH_2$ | H | $n\text{-}C_3H_7$ | allyl | 62–64 |
| 22 | $CH_2SCH_2SCH_2$ | H | $C_2H_5$ | 3-chloroallyl (trans) | |
| 23 | $CH_2SCH_2SCH_2$ | H | $n\text{-}C_3H_7$ | 3-chloroallyl (trans) | |
| 24 | $CH_2CH_2SCH_2CH_2$ | H | $n\text{-}C_3H_7$ | $C_2H_5$ | 1.5508 (23) |
| 25 | $CH_2CH_2SCH_2CH_2$ | H | $n\text{-}C_3H_7$ | 3-chloroallyl (trans) | |
| 26 | $CH_2CH_2SCH_2CH_2$ | H | $n\text{-}C_3H_7$ | allyl | 1.5558 (23) |
| 27 | $CH_2OCH_2CH_2CH_2$ | H | $n\text{-}C_3H_7$ | 3-Cl—allyl (trans) | |
| 28 | $CH_2OCH_2CH_2CH_2$ | H | $n\text{-}C_3H_7$ | methylallyl (trans) | |
| 29 | $CH_2OCH_2CH_2CH_2$ | H | $C_2H_5$ | $C_2H_5$ | |
| 30 | $CH_2OCH_2CH_2CH_2$ | H | $C_2H_5$ | allyl | |
| 31 | $CH_2OCH_2CH_2CH_2$ | H | $C_2H_5$ | 3-Cl—allyl (trans) | |
| 32 | $CH_2OCH_2CH_2CH_2$ | H | $C_2H_5$ | methylallyl (trans) | |
| 33 | $CH_2CH_2OCH_2CH_2$ | H | $n\text{-}C_3H_7$ | 3-Cl—allyl (trans) | |
| 34 | $CH_2CH_2OCH_2CH_2$ | H | $n\text{-}C_3H_7$ | methylallyl (trans) | |
| 35 | $CH_2CH_2OCH_2CH_2$ | H | $C_2H_5$ | $C_2H_5$ | |
| 36 | $CH_2CH_2OCH_2CH_2$ | H | $C_2H_5$ | allyl | |
| 37 | $CH_2CH_2OCH_2CH_2$ | H | $C_2H_5$ | 3-Cl—allyl (trans) | |
| 38 | $CH_2CH_2OCH_2CH_2$ | H | $C_2H_5$ | methylallyl (trans) | |
| 39 | $CH_2SCH_2CH_2CH_2$ | H | $n\text{-}C_3H_7$ | methylallyl (trans) | |
| 40 | $CH_2SCH_2CH_2CH_2$ | H | $C_2H_5$ | $C_2H_5$ | |
| 41 | $CH_2SCH_2CH_2CH_2$ | H | $C_2H_5$ | allyl | |
| 42 | $CH_2SCH_2CH_2CH_2$ | H | $C_2H_5$ | 3-Cl—allyl (trans) | |
| 43 | $CH_2SCH_2CH_2CH_2$ | H | $C_2H_5$ | methylallyl (trans) | |
| 44 | $SCH_2CH_2CH_2CH_2$ | H | $n\text{-}C_3H_7$ | $C_2H_5$ | |
| 45 | $SCH_2CH_2CH_2CH_2$ | H | $n\text{-}C_3H_7$ | allyl | |
| 46 | $SCH_2CH_2CH_2CH_2$ | H | $n\text{-}C_3H_7$ | 3-Cl—allyl (trans) | |
| 47 | $SCH_2CH_2CH_2CH_2$ | H | $n\text{-}C_3H_7$ | methylallyl (trans) | |
| 48 | $SCH_2CH_2CH_2CH_2$ | H | $C_2H_5$ | $C_2H_5$ | |
| 49 | $SCH_2CH_2CH_2CH_2$ | H | $C_2H_5$ | allyl | |
| 50 | $SCH_2CH_2CH_2CH_2$ | H | $C_2H_5$ | 3-Cl—allyl (trans) | |
| 51 | $SCH_2CH_2CH_2CH_2$ | H | $C_2H_5$ | methylallyl (trans) | |
| 52 | $CH_2CH_2SCH_2CH_2$ | H | $n\text{-}C_3H_7$ | 3-Cl—allyl (trans) | |
| 53 | $CH_2CH_2SCH_2CH_2$ | H | $n\text{-}C_3H_7$ | methylallyl (trans) | |
| 54 | $CH_2CH_2SCH_2CH_2$ | H | $C_2H_5$ | $C_2H_5$ | |
| 55 | $CH_2CH_2SCH_2CH_2$ | H | $C_2H_5$ | allyl | |
| 56 | $CH_2CH_2SCH_2CH_2$ | H | $C_2H_5$ | 3-Cl—allyl (trans) | |
| 57 | $CH_2CH_2SCH_2CH_2$ | H | $C_2H_5$ | methylallyl (trans) | |
| 58 | $CH_2OCH_2OCH_2$ | H | $n\text{-}C_3H_7$ | $C_2H_5$ | |
| 59 | $CH_2OCH_2OCH_2$ | H | $n\text{-}C_3H_7$ | allyl | |
| 60 | $CH_2OCH_2OCH_2$ | H | $n\text{-}C_3H_7$ | 3-Cl—allyl (trans) | |
| 61 | $CH_2OCH_2OCH_2$ | H | $n\text{-}C_3H_7$ | methylallyl (trans) | |
| 62 | $CH_2OCH_2OCH_2$ | H | $C_2H_5$ | $C_2H_5$ | |
| 63 | $CH_2OCH_2OCH_2$ | H | $C_2H_5$ | allyl | |
| 64 | $CH_2OCH_2OCH_2$ | H | $C_2H_5$ | 3-Cl—allyl (trans) | |
| 65 | $CH_2OCH_2OCH_2$ | H | $C_2H_5$ | methylallyl (trans) | |
| 66 | $CH_2SCH_2SCH_2$ | H | $n\text{-}C_3H_7$ | 3-Cl—allyl (trans) | |
| 67 | $CH_2SCH_2SCH_2$ | H | $n\text{-}C_3H_7$ | methylallyl (trans) | |
| 68 | $CH_2SCH_2SCH_2$ | H | $C_2H_5$ | 3-Cl—allyl (trans) | |
| 69 | $CH_2SCH_2SCH_2$ | H | $C_2H_5$ | methylallyl (trans) | |
| 70 | $CH_2CH(OCH_3)CH_2CH_2CH_2$ | H | $n\text{-}C_3H_7$ | $C_2H_5$ | |
| 71 | $CH_2CH(OCH_3)CH_2CH_2CH_2$ | H | $n\text{-}C_3H_7$ | allyl | |
| 72 | $CH_2CH(OCH_3)CH_2CH_2CH_2$ | H | $n\text{-}C_3H_7$ | 3-Cl—allyl (trans) | |
| 73 | $CH_2CH(OCH_3)CH_2CH_2CH_2$ | H | $n\text{-}C_3H_7$ | methylallyl (trans) | |
| 74 | $CH_2CH(OCH_3)CH_2CH_2CH_2$ | H | $C_2H_5$ | $C_2H_5$ | |
| 75 | $CH_2CH(OCH_3)CH_2CH_2CH_2$ | H | $C_2H_5$ | allyl | |

-continued

| Compound no. | X | Z | $R^1$ | $R^2$ | M.p.[°C.]/$n_D$ (°C.)/$^1$H—NMR data |
|---|---|---|---|---|---|
| 76 | $CH_2CH(OCH_3)CH_2CH_2CH_2$ | H | $C_2H_5$ | 3-Cl—allyl (trans) | |
| 77 | $CH_2CH(OCH_3)CH_2CH_2CH_2$ | H | $C_2H_5$ | methylallyl (trans) | |
| 78 | $CH_2CH_2CH(OCH_3)CH_2CH_2$ | H | $n\text{-}C_3H_7$ | $C_2H_5$ | |
| 79 | $CH_2CH_2CH(OCH_3)CH_2CH_2$ | H | $n\text{-}C_3H_7$ | allyl | |
| 80 | $CH_2CH_2CH(OCH_3)CH_2CH_2$ | H | $n\text{-}C_3H_7$ | 3-Cl—allyl (trans) | |
| 81 | $CH_2CH_2CH(OCH_3)CH_2CH_2$ | H | $n\text{-}C_3H_7$ | methylallyl (trans) | |
| 82 | $CH_2CH_2CH(OCH_3)CH_2CH_2$ | H | $C_2H_5$ | $C_2H_5$ | |
| 83 | $CH_2CH_2CH(OCH_3)CH_2CH_2$ | H | $C_2H_5$ | allyl | |
| 84 | $CH_2CH_2CH(OCH_3)CH_2CH_2$ | H | $C_2H_5$ | 3-Cl—allyl (trans) | |
| 85 | $CH_2CH_2CH(OCH_3)CH_2CH_2$ | H | $C_2H_5$ | methylallyl (trans) | |
| 86 | $CH(SCH_3)CH_2CH_2CH_2CH_2$ | H | $n\text{-}C_3H_7$ | $C_2H_5$ | |
| 87 | $CH(SCH_3)CH_2CH_2CH_2CH_2$ | H | $n\text{-}C_3H_7$ | allyl | |
| 88 | $CH(SCH_3)CH_2CH_2CH_2CH_2$ | H | $n\text{-}C_3H_7$ | 3-Cl—allyl (trans) | |
| 89 | $CH(SCH_3)CH_2CH_2CH_2CH_2$ | H | $n\text{-}C_3H_7$ | methylallyl (trans) | |
| 90 | $CH(SCH_3)CH_2CH_2CH_2CH_2$ | H | $C_2H_5$ | $C_2H_5$ | |
| 91 | $CH(SCH_3)CH_2CH_2CH_2CH_2$ | H | $C_2H_5$ | allyl | |
| 92 | $CH(SCH_3)CH_2CH_2CH_2CH_2$ | H | $C_2H_5$ | 3-Cl—allyl (trans) | |
| 93 | $CH(SCH_3)CH_2CH_2CH_2CH_2$ | H | $C_2H_5$ | methylallyl (trans) | |
| 94 | $CH_2CH(SCH_3)CH_2CH_2CH_2$ | H | $n\text{-}C_3H_7$ | $C_2H_5$ | |
| 95 | $CH_2CH(SCH_3)CH_2CH_2CH_2$ | H | $n\text{-}C_3H_7$ | allyl | |
| 96 | $CH_2CH(SCH_3)CH_2CH_2CH_2$ | H | $n\text{-}C_3H_7$ | 3-Cl—allyl (trans) | |
| 97 | $CH_2CH(SCH_3)CH_2CH_2CH_2$ | H | $n\text{-}C_3H_7$ | methylallyl (trans) | |
| 98 | $CH_2CH(SCH_3)CH_2CH_2CH_2$ | H | $C_2H_5$ | $C_2H_5$ | |
| 99 | $CH_2CH(SCH_3)CH_2CH_2CH_2$ | H | $C_2H_5$ | allyl | |
| 100 | $CH_2CH(SCH_3)CH_2CH_2CH_2$ | H | $C_2H_5$ | 3-Cl—allyl (trans) | |
| 101 | $CH_2CH(SCH_3)CH_2CH_2CH_2$ | H | $C_2H_5$ | methylallyl (trans) | |
| 102 | $CH_2CH(SCH_2CH_3)CH_2CH_2CH_2$ | H | $n\text{-}C_3H_7$ | 3-Cl—allyl (trans) | |
| 103 | $CH_2CH(SCH_2CH_3)CH_2CH_2CH_2$ | H | $n\text{-}C_3H_7$ | methylallyl (trans) | |
| 104 | $CH_2CH(SCH_2CH_3)CH_2CH_2CH_2$ | H | $C_2H_5$ | $C_2H_5$ | |
| 105 | $CH_2CH(SCH_2CH_3)CH_2CH_2CH_2$ | H | $C_2H_5$ | allyl | |
| 106 | $CH_2CH(SCH_2CH_3)CH_2CH_2CH_2$ | H | $C_2H_5$ | 3-Cl—allyl (trans) | |
| 107 | $CH_2CH(SCH_2CH_3)CH_2CH_2CH_2$ | H | $C_2H_5$ | methylallyl (trans) | |
| 108 | $CH_2CH(SOCH_3)CH_2CH_2CH_2$ | H | $n\text{-}C_3H_7$ | $C_2H_5$ | |
| 109 | $CH_2CH(SOCH_3)CH_2CH_2CH_2$ | H | $n\text{-}C_3H_7$ | allyl | |
| 110 | $CH_2CH(SOCH_3)CH_2CH_2CH_2$ | H | $n\text{-}C_3H_7$ | 3-Cl—allyl (trans) | |
| 111 | $CH_2CH(SOCH_3)CH_2CH_2CH_2$ | H | $n\text{-}C_3H_7$ | methylallyl (trans) | |
| 112 | $CH_2CH(SOCH_3)CH_2CH_2CH_2$ | H | $C_2H_5$ | $C_2H_5$ | |
| 113 | $CH_2CH(SOCH_3)CH_2CH_2CH_2$ | H | $C_2H_5$ | allyl | |
| 114 | $CH_2CH(SOCH_3)CH_2CH_2CH_2$ | H | $C_2H_5$ | 3-Cl—allyl (trans) | |
| 115 | $CH_2CH(SOCH_3)CH_2CH_2CH_2$ | H | $C_2H_5$ | methylallyl (trans) | |
| 116 | $CH_2CH(SO_2CH_3)CH_2CH_2CH_2$ | H | $n\text{-}C_3H_7$ | $C_2H_5$ | |
| 117 | $CH_2CH(SO_2CH_3)CH_2CH_2CH_2$ | H | $n\text{-}C_3H_7$ | allyl | |
| 118 | $CH_2CH(SO_2CH_3)CH_2CH_2CH_2$ | H | $n\text{-}C_3H_7$ | 3-Cl—allyl (trans) | |
| 119 | $CH_2CH(SO_2CH_3)CH_2CH_2CH_2$ | H | $n\text{-}C_3H_7$ | methylallyl (trans) | |
| 120 | $CH_2CH(SO_2CH_3)CH_2CH_2CH_2$ | H | $C_2H_5$ | $C_2H_5$ | |
| 121 | $CH_2CH(SO_2CH_3)CH_2CH_2CH_2$ | H | $C_2H_5$ | allyl | |
| 122 | $CH_2CH(SO_2CH_3)CH_2CH_2CH_2$ | H | $C_2H_5$ | 3-Cl—allyl (trans) | |
| 123 | $CH_2CH(SO_2CH_3)CH_2CH_2CH_2$ | H | $C_2H_5$ | methylallyl (trans) | |
| 124 | $CH_2CH_2N(COCH_3)CH_2CH_2$ | H | $n\text{-}C_3H_7$ | $C_2H_5$ | |
| 125 | $CH_2CH_2N(COCH_3)CH_2CH_2$ | H | $n\text{-}C_3H_7$ | allyl | |
| 126 | $CH_2CH_2N(COCH_3)CH_2CH_2$ | H | $n\text{-}C_3H_7$ | 3-Cl—allyl (trans) | |
| 127 | $CH_2CH_2N(COCH_3)CH_2CH_2$ | H | $n\text{-}C_3H_7$ | methylallyl (trans) | |
| 128 | $CH_2CH_2N(COCH_3)CH_2CH_2$ | H | $C_2H_5$ | $C_2H_5$ | |
| 129 | $CH_2CH_2N(COCH_3)CH_2CH_2$ | H | $C_2H_5$ | allyl | |
| 130 | $CH_2CH_2N(COCH_3)CH_2CH_2$ | H | $C_2H_5$ | 3-Cl—allyl (trans) | |
| 131 | $CH_2CH_2N(COCH_3)CH_2CH_2$ | H | $C_2H_5$ | methylallyl (trans) | |
| 132 | $CH_2CH_2N(COC_6H_5)CH_2CH_2$ | H | $n\text{-}C_3H_7$ | $C_2H_5$ | 83–85 |
| 133 | $CH_2CH_2N(COC_6H_5)CH_2CH_2$ | H | $n\text{-}C_3H_7$ | allyl | |
| 134 | $CH_2CH_2N(COC_6H_5)CH_2CH_2$ | H | $n\text{-}C_3H_7$ | 3-Cl—allyl (trans) | |
| 135 | $CH_2CH_2N(COC_6H_5)CH_2CH_2$ | H | $n\text{-}C_3H_7$ | methylallyl (trans) | |
| 136 | $CH_2CH_2N(COC_6H_5)CH_2CH_2$ | H | $C_2H_5$ | $C_2H_5$ | |
| 137 | $CH_2CH_2N(COC_6H_5)CH_2CH_2$ | H | $C_2H_5$ | allyl | |
| 138 | $CH_2CH_2N(COC_6H_5)CH_2CH_2$ | H | $C_2H_5$ | 3-Cl—allyl (trans) | |
| 139 | $CH_2CH_2N(COC_6H_5)CH_2CH_2$ | H | $C_2H_5$ | methylallyl (trans) | |
| 140 | $CH_2CH_2N(COC_6H_5)CH_2CH_2$ | $CO_2CH_3$ | $n\text{-}C_3H_7$ | $C_2H_5$ | 55–57° C. |
| 141 | $CH_2CH_2N(COCH_3)CH_2CH_2$ | $CO_2CH_3$ | $n\text{-}C_3H_7$ | $C_2H_5$ | 0.98 (t, 3H), 1.35 (t, 3H), 1.47–1.74 (m, 6H), 2.09 (s, 3H), 2.87–3.0 (m, 2H), 3.32–3.6 (m, 2H), 3.72 (s, 3H), 4.1 (q, 2H) |
| 142 | $CH_2CH_2CH(SCH_3)CH_2CH_2$ | H | $n\text{-}C_3H_7$ | $C_2H_5$ | |
| 143 | $CH_2CH_2CH(SCH_3)CH_2CH_2$ | H | $n\text{-}C_3H_7$ | allyl | |
| 144 | $CH_2CH_2CH(SCH_3)CH_2CH_2$ | H | $n\text{-}C_3H_7$ | 3-Cl—allyl (trans) | |
| 145 | $CH_2CH_2CH(SCH_3)CH_2CH_2$ | H | $n\text{-}C_3H_7$ | methylallyl (trans) | |
| 146 | $CH_2CH_2CH(SCH_3)CH_2CH_2$ | H | $C_2H_5$ | $C_2H_5$ | |
| 147 | $CH_2CH_2CH(SCH_3)CH_2CH_2$ | H | $C_2H_5$ | allyl | |
| 148 | $CH_2CH_2CH(SCH_3)CH_2CH_2$ | H | $C_2H_5$ | 3-Cl—allyl (trans) | |
| 149 | $CH_2CH_2CH(SCH_3)CH_2CH_2$ | H | $C_2H_5$ | methylallyl (trans) | |

The cyclohexenones of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 8 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 2 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 9 is intimately mixed with 97 parts by weight of particulate kaolin. A dust is obtained containing 3% by weight of the active ingredient.

VII. 30 parts by weight of compound no. 9 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 3 kg/ha and more, but is preferably from 0.1 to 0.5 kg/ha.

The action of the cyclohexenones of the formula I on plant growth is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds are emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.125 and 0.25 kg of active ingredient per hectare. No covers were placed on the vessels in this method.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatment assessed. The scale used for assessment was 0 to 100, 0 denoting no damage or normal emergence, and 100 denoting nonemergence or complete destruction of at least the visible plant parts.

The plants used in the experiments were *Avena fatua, Avena sativa, Digitaria sanguinalis, Echinochloa crusgalli, Glycine max., Hordeum vulgare, Lolium multiflorum, Oryza sativa, Setaria italica,* and *Sinapis alba.*

For comparative purposes, herbicides were used which contained the active ingredients 3-(1-ethoxyimino-n-butyl)-spiro[5.5]-undecane-2,4-dione (A; Japanese Laid-Open Application No. 82/183 746) or 8-(1-ethoxyimino-n-butyl)-2-thiaspiro[4.5]-decane-7,9-dione (B; Japanese Laid-Open Application No. 83/144 348).

Preemergence application

For instance compounds nos. 1, 2, 6, 8 and 9 proved to be herbicidally effective on plants from the grasses family, whereas *Sinapis alba,* as a representative of dicotyledonous plants, remained completely undamaged.

Postemergence application

On postemergence application of 0.125 kg/ha, for example compounds nos. 1 and 2 combatted grassy plants better than comparative agent A; soybeans, as dicotyledonous crop plant, were not damaged. For instance compounds nos. 6 and 8 are better tolerated than comparative agent B in combatting unwanted grasses in rice, a crop from the grasses family.

Significant problem weeds in soybeans can be better combatted with compounds nos. 24 and 26 than with prior art active ingredient A, and the broadleaved crop plant suffers no damage. Compounds nos. 20 and 21, for instance, are suitable for use against volunteer plants from the Graminease family, such as *Sorghum bicolor* and *Zea mays,* and against important grassy weeds in soybeans. Comparative agent A has a far inferior herbicidal action.

In view of their spectrum of action, their tolerance by crop plants or the desired influence on crop plant growth, and in view of the numerous application methods possible, the compounds according to the invention may be used in a large number of crop plants.

The following crops may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Phaseolus lunatus* | limabeans |
| *Phaseolus mungo* | mungbeans |

| Botanical name | Common name |
| --- | --- |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenones of the formula I may be mixed with each other, and mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinoline-carboxylic acids, cyclohexenones of a different structure, etc.

It may also be useful to apply the cyclohexenones of the formula I, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone of the formula

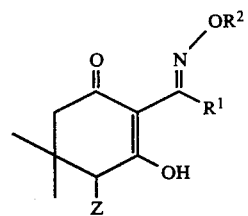

where $R^1$ is $C_1$–$C_4$-alkyl, $R^2$ is $C_1$–$C_4$-alkyl, $C_3$–$C_5$-alkynyl or unsubstituted or halogen-substituted $C_3$–$C_5$-alkenyl, Z is hydrogen or $C_2$–$C_5$-alkoxycarbonyl and X is an oxapentamethylene chain.

2. A cyclohexenone of the formula I as set forth in claim 1, where Z is hydrogen.

3. 9-(1-Ethoxyimino-n-butyl)-3-oxaspiro[5,5]-undecane-8,10-dione.

4. A herbicide containing inert additives and an effective amount of a cyclohexenone of the formula I as set forth in claim 1.

5. A herbicide as set forth in claim 4, containing from 0.1 to 95 wt% of a cyclohexenone of the formula I.

6. A process for combatting the growth of unwanted plants, wherein the unwanted plants or the area to be kept free from unwanted plant growth are treated with a herbicidally effective amount of a cyclohexenone of the formula I as set forth in claim 1.

7. A process as set forth in claim 6, wherein the cyclohexenone of the formula I is applied at a rate of from 0.025 to 3 kg/ha.

* * * * *